United States Patent [19]

Simon

[11] 4,336,387
[45] Jun. 22, 1982

[54] THIAZOLIDINE-SUBSTITUTED PHENYL SULFONYL CHLORIDES

[75] Inventor: Myron S. Simon, West Newton, Mass.

[73] Assignee: Polaroid Corporation, Cambridge, Mass.

[21] Appl. No.: 239,358

[22] Filed: Mar. 2, 1981

[51] Int. Cl.$^3$ .............................................. C07N 277/04
[52] U.S. Cl. .................................................. 548/146
[58] Field of Search ................................ 548/146, 148

[56] References Cited

U.S. PATENT DOCUMENTS

| | | | |
|---|---|---|---|
| 2,112,445 | 3/1938 | Niederl | 548/146 |
| 3,108,114 | 10/1963 | Krespan | 548/146 |
| 3,719,489 | 3/1973 | Cieciuch et al. | 548/146 |
| 3,816,445 | 6/1974 | Dubs et al. | 548/146 |
| 4,098,783 | 7/1978 | Cieciuch et al. | 548/146 |

FOREIGN PATENT DOCUMENTS 2202369  7/1973  Fed. Rep. of Germany ...... 548/146

OTHER PUBLICATIONS

*Chemical Abstracts*, vol. 66, #70866y, Agbo et al., 10/25/66, "Printing Material Prepared by Using Photoinsoulubilizable Polymers".
*The Chemistry of Penicillin*, H. Clarke, Ed., 1949, pp. 926–928, 932 and 949.
*Chem. Ber.*, vol. 90, No. 6, Meerwein et al., 1957, p. 841.

*Primary Examiner*—Thomas A. Waltz
*Assistant Examiner*—Raymond Covington
*Attorney, Agent, or Firm*—Sybil A. Campbell

[57] ABSTRACT

This invention is concerned with certain 3-(thiazolidin-2'-yl)-substituted phenyl sulfonyl chlorides which find utility as intermediates in the preparation of photographic image dye-providing materials.

8 Claims, No Drawings

THIAZOLIDINE-SUBSTITUTED PHENYL SULFONYL CHLORIDES

1. Field of the Invention

This invention relates to certain 3-(thiazolidin-2'-yl)-substituted phenyl sulfonyl chlorides useful as intermediates in the preparation of photographic image dye-providing materials.

2. Background of the Invention

U.S. Pat. No. 3,719,489 describes and claims photographic processes employing certain photographically inert compounds which are capable of undergoing cleavage in the presence of the imagewise distribution of silver ions made available during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color-providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Compounds disclosed as useful in liberating a reagent in the presence of said silver ions and/or silver complex are sulfur-nitrogen compounds containing the group $$-S-X-N-$$

or —S—X—N=wherein X is

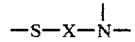

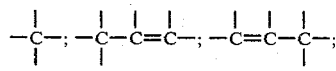

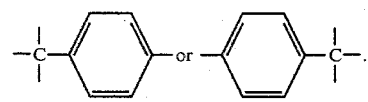

These 1,3-sulfur-nitrogen compounds may be linear or cyclic in structure, and in a particularly preferred embodiment are thiazolidine compounds, such as, compounds which comprise a dye radical having the chromophoric system of an azo, anthraquinone, phthalocyanine or other dye and a thiazolidin-2'-yl moiety which may be bonded directly to the dye radical or through an appropriate linking group.

U.S. Pat. No. 4,098,783, a continuation-in-part of Ser. No. 465,694, now abandoned, which is a division of said U.S. Pat. No. 3,719,489 discloses that dyes substituted with a thiazolidin-2'-yl moiety may be synthesized by condensing a dye possessing an aldehyde group with a 2-aminoethanethiol, or rather than forming the thiazolidin-2'-yl moiety as the final step in the synthesis, an intermediate possessing an aldehyde group may be condensed with the selected 2-aminoethanethiol and the condensation product then reacted with the appropriate molecule or molecules to yield the final dye product. For example, an intermediate comprising a linking group substituted with a thiazolidin-2'-yl moiety may be synthesized from a selected aldehyde in several steps including the condensation with a 2-aminoethanethiol and the linking group then reacted as an amine with a dye radical possessing, e.g., a sulfonyl chloride substituent or it may be reacted as a sulfonyl chloride with a dye radical possessing an amino substituent.

A process of preparing aromatic sulfonyl chlorides by a modification of the Sandmeyer reaction has been reported by Hans Meerwein et al., Chem. Ber., Vol. 90, No. 6, p. 841 (1957). In the method described, a concentrated solution of a diazonium chloride in hydrochloric acid is stirred into a saturated solution of sulfur dioxide in glacial acetic acid containing copper(I)chloride as catalyst or preferably, copper(II)chloride dihydrate which is reduced to copper(I)chloride by the sulfur dioxide. Depending upon the particular diazonium chloride, the reaction is accelerated and yields increased by adding metal chlorides, particularly magnesium chloride, to increase the chloride ion concentration. Substantially the same effect is achieved by adding a water-immiscible solvent with a low dielectric constant in a quantity such that a two-phase reaction mixture is formed. Employing this general method, the diazonium chlorides of aniline compounds, such as, chloroanilines, toluidines, anisidines, m-aminobenzoic acid, anthranilic acid methyl ester and p-aminobenzoic acid methyl ester were converted to the corresponding sulfonyl chlorides.

The present invention is concerned with certain 3-(thiazolidin-2'-yl)-substituted phenyl sulfonyl chlorides.

SUMMARY OF THE INVENTION

It is, therefore, the primary object of the present invention to provide novel phenyl sulfonyl chlorides possessing a thiazolidin-2'-yl substituent.

Other objects of the present invention will in part be obvious and will in part appear hereinafter.

The invention accordingly comprises the products and compositions possessing the features, properties and relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

Specifically, the 3-(thiazolidin-2'-yl)-substituted phenyl sulfonyl chlorides of the present invention may be represented by the formula

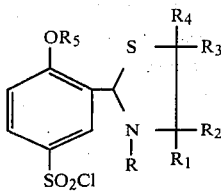

wherein R is selected from alkyl, usually containing 1 to 20 carbon atoms, aryl, e.g., phenyl and aralkyl, e.g., phenyl-substituted alkyl, usually alkyl containing 1 to 20 carbon atoms; $R_1$, $R_2$, $R_3$ and $R_4$ each are selected from hydrogen, alkyl, usually containing 1 to 20 carbon atoms, and phenyl; and $R_5$ is hydrogen or acyl. The alkyl, aryl and aralkyl groups comprising R, $R_1$, $R_2$, $R_3$ and $R_4$ may be unsubstituted or substituted with a group, such as, halogens, alkoxy and hydroxy. Preferably, when R is alkyl, it contains at least 10 carbon atoms, i.e., 10 to 20 carbon atoms. $R_5$ may be any acyl groups, e.g., acetyl, benzoyl or tosyl.

It now has been found that a thiazolidin-2'-yl substituted aniline can be converted to the corresponding sulfonyl chloride using the modification of the Sandmeyer reaction described above. It is quite unexpected and indeed, surprising that the desired thiazolidin-2'-yl substituted phenyl sulfonyl chloride product is obtained in the presence of strong mineral acid, the copper catalyst and nitrous acid, since it is known that the thiazolidine ring is subject to decomposition in the presence of acids or metal ions and that the sulfur atom of the ring is subject to oxidation to the sulfoxide or sulfone. For example, the cleavage of the thiazolidine ring with HCl is discussed in *The Chemistry of Penicillins*, H. Clarke, Ed., 1949, at pages 932 and 949. The reaction of thiazolidine rings with metal ions including $Cu^{++}$ is discussed at pages 926 and 927 of this text, and the oxidation of the thiazolidine ring is discussed at p. 928 and in the references cited therein.

The 3-(thiazolidin-2'-yl)-4-acyloxy-anilines employed as the starting materials in preparing the subject compounds are known and may be synthesized as described in aforementioned U.S. Pat. No. 4,098,783 by reacting 5-nitrosalicylaldehyde with the selected 2-aminoethanethiol to give the corresponding 2-(2'-hydroxy-5'-nitrophenyl)-thiazolidine followed by protecting said hydroxy group by reacting with an acid chloride, and then reducing said nitro group to give the 3-(thiazolidin-2'-yl)-4-acyloxy-aniline. The 2-aminoethanethiols employed in synthesizing the thiazolidinyl-substituted anilines may be prepared in various ways, for example, by the mercaptoethylation of amines and ammonia with episulfides as disclosed and claimed in U.S. Pat. No. 3,919,277.

The following example is given to further illustrate the present invention and is not intended to limit the scope thereof.

EXAMPLE

Preparation of the compound having the formula

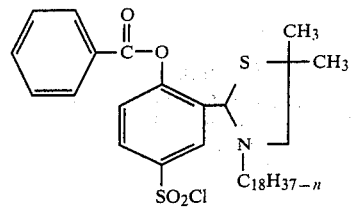

3-(5',5'-dimethyl-3'-n-octadecyl-thiazolidin-2'-yl)-4-benzoyloxy-aniline (100 gms., 0.17 mole) was dissolved in 850 ml of glacial acetic acid and stirred mechanically. To this solution was added 35 ml conc. hydrochloric acid (ca. 0.42 mole) and the resulting solution cooled in an ice water bath. A solution of sodium nitrite (12 gms., 0.17 mole) in 20 ml of water was added dropwise. After the addition was complete, it was noted that the internal temperature of the reaction solution was $+10°$ C.

While this diazotization solution was stirred with ice bath cooling, 400 ml of glacial acetic acid was saturated with sulfur dioxide ($SO_2$) in a 2 liter flask.

After a period of 0.6 hour, approximately 1 gm. of urea was added to the cooled diazotization solution, followed by 24 gms. of $MgCl_2 \cdot XH_2O$. The sulfur dioxide saturated acetic acid solution was warmed to 32° C. with a water bath, and 24 gms. of $CuCl_2 \cdot 2H_2O$ was added. (Sulfur dioxide was bubbled into the glacial acetic acid continuously.) With rapid mechanical stirring of the glacial acetic acid/$SO_2CuCl_2$ solution, the diazo solution and any insoluble material with it was poured in all at once. The water bath was adjusted to 47° C. and was allowed to cool gradually to room temperature. After two and one-half hours, 1500 ml of water was added and the solution was extracted two times with ether. The combined ether extracts were washed four times with aqueous sodium chloride solution, dried with magnesium sulfate and concentrated. The pale orange solid residue was dried under high vacuum to remove glacial acetic acid and then crystallized from one liter of hexane to give 74 gms., 65% by weight yield of the title compound. (melting range 77°–79° C.)

The corresponding 3-(5',5'-dimethyl-3'-n-octadecyl-thiazolidin-2'-yl)-4-hydroxy-phenyl sulfonyl chloride may be prepared from the compound produced in the Example by selective hydrolysis. The corresponding 4-hydroxy-phenyl sulfonyl chloride also may be synthesized by reacting the thiazolidinyl-substituted 4-hydroxy-phenyl sulfonic acid with thionyl chloride as disclosed and claimed in copending U.S. Patent application Ser. No. 239,356 of Charles A. Kelly and Frank A. Meneghini filed concurrently herewith.

As mentioned previously, the subject compounds are useful as intermediates in the synthesis of photographic image dye-providing materials. For instance, they may be employed as intermediates in the preparation of thiazolidine-substituted dye image-providing materials as described in aforementioned U.S. Pat. No. 4,098,783. For this purpose, they may be reacted with a dye substituted with an amino group to yield the image dye-providing material, or they may be reacted with one amino group of an alkylene diamine and the reaction product reacted with a dye substituted with, e.g., a —COCl or —$SO_2Cl$ group to give the image dye-providing material. As an example, the compound having the formula

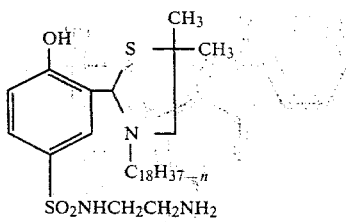

Compound A was prepared as follows:

To a stirring, cooled (0° C.) solution of 225.6 g ethylene diamine in 1000 ml of tetrahydrofuran (THF) under nitrogen, was added a solution containing 50 g of the compound of the Example in 250 ml of tetrahydrofuran, dropwise, under nitrogen, over a period of 1–2 hours. The reaction mixture was allowed to stir overnight and the temperature allowed to come to room temperature (25° C.). The resulting solution was a cloudy yellow color with a small THF insoluble oil at the bottom of the flask. The solvent was removed by vacuum evaporation at 40° C. leaving a dark yellow brown viscous oil. To this oil was added ether and the mixture was added to a separatory funnel with ice/water mixture, washed, brined and dried over sodium sulfate to yield 49.0 g of the title compound as a clear viscous yellow orange oil.

The dihydrochloride salt of the above sulfonamide was prepared as follows:

To 80 ml of dry dichloromethane stirred at −5° to 0° C. was added 9.04 g (150 mmoles) of ethylenediamine. To the solution was added 2.00 g (3.30 mmoles) of 3-(5′,5′-dimethyl-3′-n-octadecyl-thiazolidin-2′-yl)-4-hydroxy-phenyl sulfonyl chloride.hydrochloride in 10 ml of dichloromethane using an addition funnel. The sulfonyl chloride was added at a rate such that the temperature remained between about 0° and 5° C. The mixture was then stirred at 0° C. for 1.5 hours. It was then extracted with 100 ml (×2) of 1 N HCl, 100 ml of water, and 100 ml of brine. The organic layer was dried over magnesium sulfate. The magnesium sulfate was removed by filtration, and 70 ml of hexane was added to the stirring dichloromethane solution. Dry HCl was slowly bubbled through the solution until no more was absorbed. The solvent was evaporated in vacuo to dryness yielding the title compound as a pale yellow solid: 1.92 g (2.80 mmoles); 85.4% by weight yield.

It will be appreciated that this sulfonamide may then be reacted with a dye possessing, e.g., a —COCl or —SO₂Cl group to give the image dye-providing material. As an illustration, 280 mgs of Compound A and 190 mgs (one equivalent) of the yellow dye of the formula

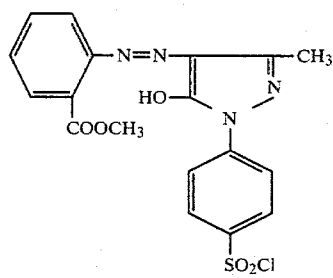

were combined in pyridine and allowed to stir overnight. The pyridine was evaporated, dilute HCl added, and the residue triturated and filtered. The residue was taken up in chloroform, dried over sodium sulfate and concentrated. The solution was applied to a Florosil column (chloroform) and eluted with chloroform and 20% acetone/chloroform to give 210 mgs of the desired image dye-providing material of the formula

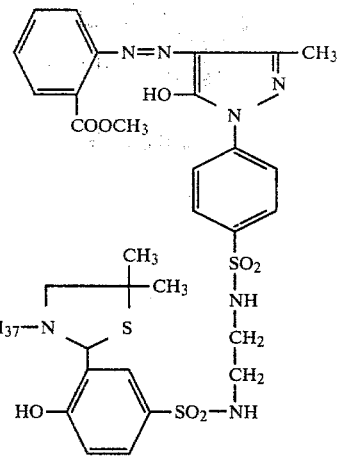

which was confirmed by nmr (CDCl₃).

Examples of other image dye-providing compounds that may be prepared from the subject intermediates are those disclosed in copending U.S. Patent application Ser. No. 143,284 of Ruth C. Bilofsky, Ronald F. Cieciuch, Louis Locatell, Jr., Howard G. Rogers and Charles M. Zepp filed Apr. 24, 1980, now U.S. Pat. No. 4,264,701 which is a continuation-in-part of U.S. Patent application Ser. No. 32,888 filed Apr. 24, 1979, now abandoned.

Since certain changes may be made in the herein described subject matter without departing from the scope of the invention herein involved, it is intended that all matter contained in the above description and examples be interpreted as illustrative and not in a limiting sense.

What is claimed is:

1. A compound of the formula

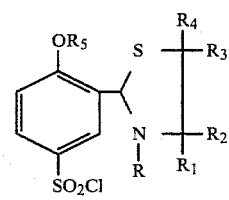

wherein R is selected from alkyl, aryl and aralkyl; $R_1$, $R_2$, $R_3$ and $R_4$ each are selected from hydrogen, alkyl and phenyl; and $R_5$ is hydrogen or acyl.

2. A compound as defined in claim 1 wherein $R_5$ is hydrogen.

3. A compound as defined in claim 1 wherein $R_5$ is acyl.

4. A compound as defined in claim 1 wherein R is alkyl.

5. A compound as defined in claim 4 wherein R is alkyl containing at least 10 carbon atoms.

6. A compound as defined in claim 5 wherein $R_3$ and $R_4$ are methyl and $R_1$ and $R_2$ are hydrogen.

7. The compound of the formula

8. The compound of the formula
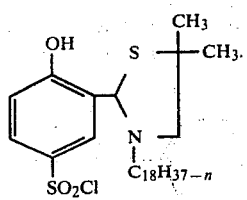
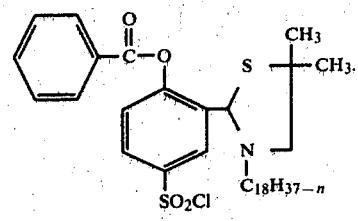
* * * * *